US00PP08765P

United States Patent [19]

Austin

[11] Patent Number: Plant 8,765

[45] Date of Patent: Jun. 7, 1994

[54] ROSE PLANT AUSLEVEL

[75] Inventor: David C. H. Austin, Albrighton, England

[73] Assignee: David Austin Roses Limited, Albrighton, England

[21] Appl. No.: 39,946

[22] Filed: Mar. 29, 1993

[30] Foreign Application Priority Data

Dec. 4, 1991 [GB] United Kingdom ..... 51397

[51] Int. Cl.[5] ..... A01H 5/00

[52] U.S. Cl. ..... Plt./1

[58] Field of Search ..... Plt. 1

*Primary Examiner*—Howard J. Locker
*Assistant Examiner*—Erich E. Veitenheimer
*Attorney, Agent, or Firm*—Klarquist Sparkman Campbell Leigh & Whinston

[57] ABSTRACT

A Rosa hybrida shrub rose is disclosed, having white, slightly creamy flowers; bushy growth; and large number of petals.

1 Drawing Sheet

The present invention relates to a new and distinct variety of rose plant (Rosa hybrida) of the shrub class which was originated by me by crossing the unpatented variety "Graham Thomas" with the unpatented variety "Mary Rose". "Graham Thomas" is characterized by having cupped, golden yellow flowers on a plant of upright habit, which is 122 cm to 152 cm tall. "Mary Rose" has rosette, rose pink flowers on a plant of bushy habit, 107 cm to 122 cm tall.

The primary objective of this breeding was to produce a new rose variety having repeat flowering with old-fashioned-type flowers. The objective was substantially achieved along with other desirable improvements as evidenced by the following unique combination of characteristics which are outstanding in the new variety and which distinguish it from its parents, as well as from all other varieties of which I am aware:

1. White, slightly creamy flowers;
2. Bushy, vegetative growth; and
3. Large number of petals.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—"Graham Thomas" variety.

*Pollen parent.13* "Mary Rose" variety.

Classification:

*Botanical.*—Rosa hybrida.

*Commercial.*—Shrub.

FLOWER

Observations made from specimens grown garden environment in Albrighton, Wolverhampton, England, in July, 1992.

Blooming habit: Recurrent.

Bud:

*Size.*—About 2.5 cm in length and about 2 cm in diameter when the petals start to unfurl.

*Form.*—Pointed ovoid.

*Color.*—When sepals first divide, bud color is yellow Group 5A. When half blown, the upper and lower sides of the petals are Yellow-Orange Group 19D, but paler.

*Sepals.*—Color: Yellow-Green Group 144A/B. Surface texture: Smooth. There are three lightly to normally appendaged sepals. There are two unappendaged sepals.

*Receptacle.*—Color: Yellow-Green Group 144B. Shape: Narrow funnel. Size: Small and slender (8–10 mm×6–7 mm). Surface: Smooth.

*Peduncle.*—Length: 4–4.5 cm. Surface: Glandular. Color: Ligth Green, slightly bronzy. Strength: Bending.

Bloom:

*Size.*—Average open size is 6–7 cm in diameter.

*Borne.*—In clusters of 2 to 4 flowers having irregular shape.

*Stems.*—Medium length, normal strength. Average length is about 60–75 cm.

*Form.*—When first open: Globular. Permanence: Flattens to form deep, open cup; outer petal edges curl slightly.

*Petalage.*—Number of petals under normal conditions: 120.

*Color.*—The upper side of the petals is Yellow Group 11D but paler (almost white) on the outer petals, and Yellow Group 11C on the inner petals. The reverse side of the outer petals is less yellow and more white than Yellow Group 11D of the outside of the upper petals, and the reverse side of the inner petals is Yellow Group 11D/C. The base of the petals is yellow slightly toward the tip. The major color on the upper side is pale Yellow Group 11D.

*Variegations.*—None.

*Discoloration.*—The general tonality at the end of the first day: Petals lose yellow tinge. At the end of the third day: Petals continue to pale toward white.

*Fragrance.*—Moderate, sweet, rich.

Petals:

*Texture.*—Silky.

*Shape.*—Notched slightly, deltoid, edges quite smooth, almost entire; tips slightly recurved.

*Form.*—Fairly flat.

*Arrangement.*—Outer petals imbricated; inner petals tucked into calyx to form button, with few petaloids in the center.

*Persistence.*—Outer petals drop off cleanly before drying.

*Lastingness.*—On the plant: About 3–4 days. As a cut flower: About 3 days.

Reproductive parts:

*Anthers.*—Size: Medium. Quantity: Many Color: Yellow. Arrangement: Mixed with petaloids.

*Filaments.*—Color: Yellow (reddish occasionally).

*Pollen.*—Color: Gold yellow.

*Styles.*—Color: White/pale green.

*Stigmas.*—Color: Yellow with pink tinge.

*Size.*—When mature, about 91 to 107 cm tall and 91 cm wide.

Form: Shrub.

Growth: Vigorous.

Foliage: Number of leaflets on normal mid-stem leaves: 7.

*Size.*—About 16–17 cm long×9–10 cm wide.

*Quantity.*—Normal.

*Color.*—New foliage: Yellow-Green Group 146A/B. Old foliage: Yellow-Green Group 147A.

Leaflets:

*Shape.*—Round, broadly oval.

*Texture.*—Upper side: Fairly smooth.

*Edge.*—Serrated.

*Serration.*—Double.

*Petiole rachis.*—Color: Reddish blush.

*Petiole underside.*—With prickles (3 to 5 prickles per internode).

*Stipules.*—About 2.5 to 3.5 cm long, broadly serrated.

*Disease resistance.*—Resistant to mildew and blackspot under normal growing conditions at Albrighton, Wolverhampton, England.

Wood:

*New wood.*—Color: Light green, reddish blush. Bark: Smooth.

*Old wood.*—Color: Green, streaky. Bark: Smooth.

Prickles:

*Quantity.*—Many on main canes from base. Ordinary quantity on laterals from main canes.

*Form.*—Medium to long in length, straight.

*Color when young.*—Pale red, transparent.

*Position.*—Evenly distributed around stems.

Small prickles:

*Quantity.*—Many on main stalks and on laterals.

*Color.*—Brown.

I claim:

1. A new and distinct variety of Rosa hybrida rose plant of the shrub class, substantially as herein shown and described, being characterized particularly as to novelty by the unique combination of its white, slightly creamy flowers; bushy growth and large number of petals.

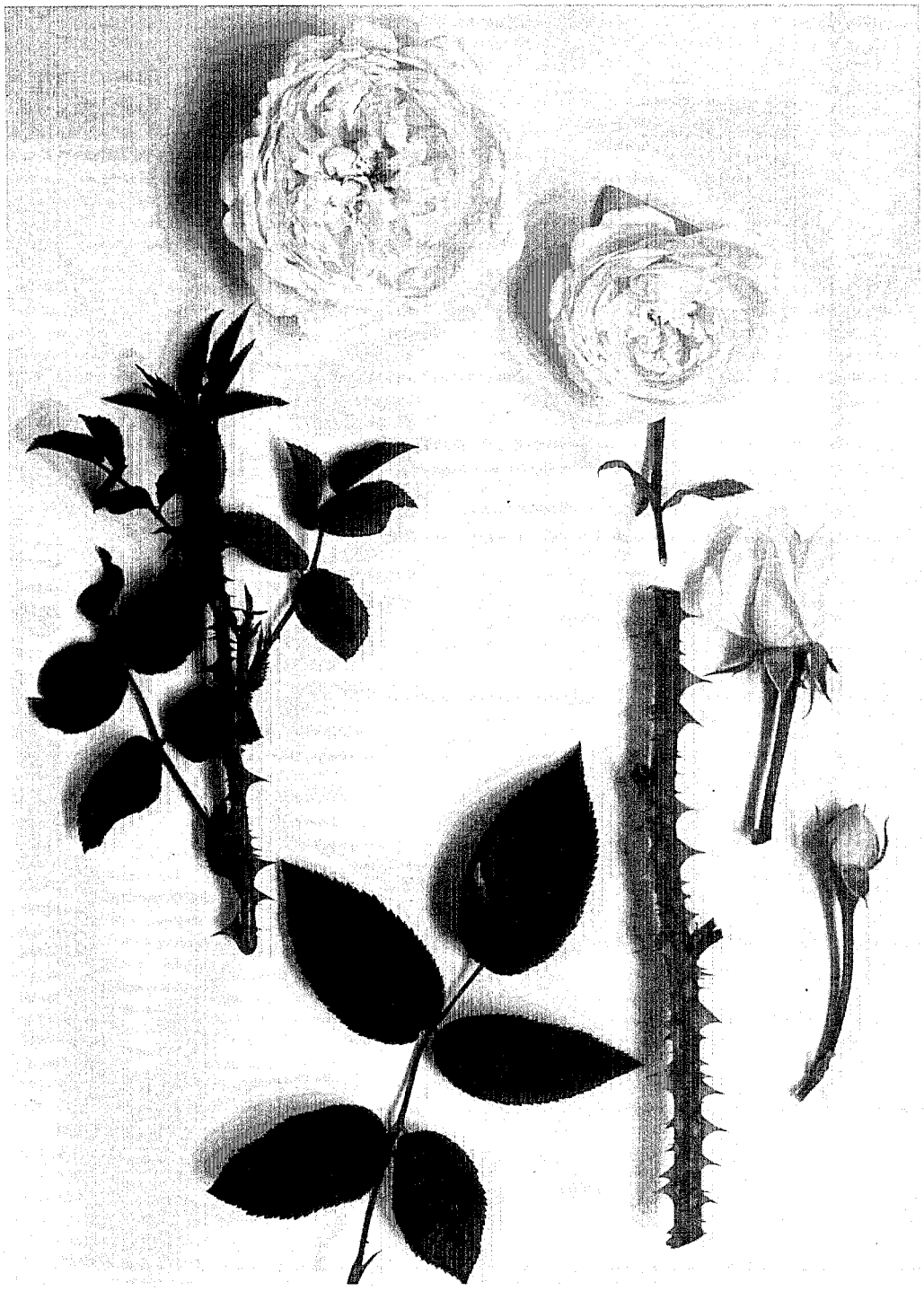

* * * * *